(12) United States Patent
Bozkurt et al.

(10) Patent No.: US 10,368,798 B2
(45) Date of Patent: Aug. 6, 2019

(54) SYSTEMS AND METHODS FOR DETERMINING SLEEP PATTERNS AND CIRCADIAN RHYTHMS

(71) Applicant: North Carolina State University, Raleigh, NC (US)

(72) Inventors: Alper Bozkurt, Raleigh, NC (US); James P. Dieffenderfer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 711 days.

(21) Appl. No.: 14/901,180

(22) PCT Filed: Jun. 29, 2014

(86) PCT No.: PCT/US2014/044775
§ 371 (c)(1),
(2) Date: Dec. 28, 2015

(87) PCT Pub. No.: WO2014/210588
PCT Pub. Date: Dec. 31, 2014

(65) Prior Publication Data
US 2016/0151012 A1  Jun. 2, 2016

Related U.S. Application Data

(60) Provisional application No. 61/840,486, filed on Jun. 28, 2013.

(51) Int. Cl.
*A61B 5/00* (2006.01)
*A61B 5/024* (2006.01)
(Continued)

(52) U.S. Cl.
CPC .......... *A61B 5/4815* (2013.01); *A61B 5/0075* (2013.01); *A61B 5/0205* (2013.01); *A61B 5/02416* (2013.01); *A61B 5/14553* (2013.01); *A61B 5/14557* (2013.01); *A61B 5/4812* (2013.01); *A61B 5/4857* (2013.01);
(Continued)

(58) Field of Classification Search
CPC .................................................. A61B 5/4821
See application file for complete search history.

(56) References Cited

U.S. PATENT DOCUMENTS 5,275,159 A   1/1994  Griebel
5,779,631 A *  7/1998  Chance .............. A61B 5/14532
                                                                600/328
(Continued)

FOREIGN PATENT DOCUMENTS

KR   10-2012-0012364    2/2012

OTHER PUBLICATIONS

International Search Report and Written Opinion for PCT Application No. PCT/US2014/044775 dated Nov. 7, 2014.

*Primary Examiner* — Michael W Kahelin
*Assistant Examiner* — Shirley X Jian
(74) *Attorney, Agent, or Firm* — Michael Best & Friedrich LLP

(57) ABSTRACT

Systems and methods for monitoring sleep are disclosed. According to an aspect, a method includes emitting light into tissue. The method also includes detecting light backscattered from the tissue. Further, the method includes determining a sleep pattern based on the backscattered light.

40 Claims, 6 Drawing Sheets

(51) Int. Cl.
*A61B 5/1455* (2006.01)
*A61B 5/0205* (2006.01)
*A61B 5/022* (2006.01)
*A61B 5/08* (2006.01)
*A61M 21/00* (2006.01)

(52) U.S. Cl.
CPC .......... *A61B 5/688* (2013.01); *A61B 5/02225* (2013.01); *A61B 5/02433* (2013.01); *A61B 5/0816* (2013.01); *A61B 2562/0238* (2013.01); *A61M 2021/0044* (2013.01)

(56) References Cited

U.S. PATENT DOCUMENTS

| | | | | |
|---|---|---|---|---|
| 5,873,821 | A * | 2/1999 | Chance | A61B 5/14532 600/310 |
| 6,526,297 | B1 * | 2/2003 | Merilainen | A61B 5/0059 600/310 |
| 6,544,193 | B2 * | 4/2003 | Abreu | A61B 3/1241 600/558 |
| 7,041,063 | B2 * | 5/2006 | Abreu | A61B 3/1241 600/549 |
| 7,047,054 | B2 * | 5/2006 | Benni | A61B 5/14552 600/310 |
| 7,169,110 | B2 * | 1/2007 | Lee | A61B 5/14551 600/481 |
| 7,248,915 | B2 * | 7/2007 | Ronnholm | A61M 21/00 340/575 |
| 7,313,427 | B2 * | 12/2007 | Benni | A61B 5/14552 600/323 |
| 7,403,805 | B2 * | 7/2008 | Abreu | A61B 3/1241 600/318 |
| 7,668,579 | B2 * | 2/2010 | Lynn | A61B 5/412 600/323 |
| 8,140,143 | B2 * | 3/2012 | Picard | A61B 5/0531 600/388 |
| 8,348,840 | B2 * | 1/2013 | Heit | A61M 21/00 600/300 |
| 8,427,311 | B2 * | 4/2013 | Schlangen | A61M 21/00 340/540 |
| 9,113,528 | B2 * | 8/2015 | Bora | H05B 33/0863 |
| 9,295,144 | B2 * | 3/2016 | Bora | H05B 33/0863 |
| 9,312,246 | B2 * | 4/2016 | Roth | C09K 11/7734 |
| 9,381,106 | B2 * | 7/2016 | Gilmer | A61F 5/0102 |
| 9,576,939 | B2 * | 2/2017 | Roth | C09K 11/7734 |
| 10,179,064 | B2 * | 1/2019 | Connor | A61F 7/0097 |
| 2002/0016536 | A1 * | 2/2002 | Benni | A61B 5/14552 600/323 |
| 2002/0049389 | A1 * | 4/2002 | Abreu | A61B 3/1241 600/558 |
| 2002/0161290 | A1 * | 10/2002 | Chance | A61B 5/14551 600/323 |
| 2004/0215095 | A1 * | 10/2004 | Lee | A61B 5/14551 600/529 |
| 2005/0190065 | A1 * | 9/2005 | Ronnholm | A61M 21/00 340/575 |
| 2006/0189855 | A1 * | 8/2006 | Moriya | A61B 5/02433 600/301 |
| 2008/0017800 | A1 * | 1/2008 | Benni | A61B 5/14552 250/339.07 |
| 2009/0227853 | A1 | 9/2009 | Wijesiriwardana et al. | |
| 2010/0049060 | A1 | 2/2010 | Schechter et al. | |
| 2010/0268056 | A1 * | 10/2010 | Picard | A61B 5/0531 600/300 |
| 2010/0277316 | A1 * | 11/2010 | Schlangen | A61M 21/00 340/540 |
| 2011/0021970 | A1 * | 1/2011 | Vo-Dinh | A61K 49/0039 604/20 |
| 2011/0124979 | A1 * | 5/2011 | Heneghan | A61B 5/024 600/301 |
| 2012/0053395 | A1 * | 3/2012 | Witt | A61B 5/0482 600/27 |
| 2012/0289869 | A1 * | 11/2012 | Tyler | A61N 7/00 601/2 |
| 2013/0172774 | A1 * | 7/2013 | Crowder | A61B 5/04 600/544 |
| 2014/0062297 | A1 * | 3/2014 | Bora | H05B 33/0863 315/34 |
| 2014/0152188 | A1 * | 6/2014 | Bora | H05B 33/0863 315/210 |
| 2015/0230959 | A1 * | 8/2015 | Gilmer | A61F 5/0102 602/17 |
| 2015/0320588 | A1 * | 11/2015 | Connor | A61F 7/0097 607/107 |
| 2016/0106950 | A1 * | 4/2016 | Vasapollo | A61M 21/02 600/27 |
| 2016/0183870 | A1 * | 6/2016 | Proud | A61B 5/4806 600/595 |
| 2016/0192876 | A1 * | 7/2016 | Proud | A61B 5/1118 600/595 |
| 2018/0070831 | A1 * | 3/2018 | Sutin | A61B 5/6814 |
| 2018/0103861 | A1 * | 4/2018 | Sutin | A61B 5/6814 |

* cited by examiner

SYSTEMS AND METHODS FOR DETERMINING SLEEP PATTERNS AND CIRCADIAN RHYTHMS

CROSS-REFERENCE TO RELATED APPLICATIONS

This application is a U.S. national stage filing under 35 U.S.C. § 371 of International Application No. PCT/US2014/044775, filed Jun. 29, 2014, which claims the benefit of and priority to U.S. Provisional Patent Application No. 61/840,486, filed Jun. 28, 2013, the entire contents of which are hereby incorporated by reference.

TECHNICAL FIELD

The present subject matter relates to medical devices. More particularly, the present subject matter relates to systems and methods for determining sleep patterns and circadian rhythms.

BACKGROUND

Studies of human sleep have revealed that sleep progresses through a series of stages. The number of stages an individual has and at which stage the individual wakes up has a direct effect on how much rest the individual will have. This is a reason why sometimes an individual can sleep only a few hours and then wake up fully rested, relaxed, and ready for a new day, and then at other times, an individual can sleep for many hours and still need more rest. It is often not recognized that by setting an alarm clock for wake up, an individual can be significantly more fully rested by sleeping another 10-20 minutes less or more than the set time for wake up. This is because the sleep stage at which an individual wakes significantly affects his or her restfulness later in the day.

It is noted that about one third of a human's life is spent sleeping. It has been reported that 62% of American adults experience a sleep problem a few nights per week, and yet a small number of people will discuss their sleep problems with their doctors. In the U.S., adults sleep an average of 6.9 hours, which is slightly less than the 7-8 hours recommended by the National Sleep Foundation. This deficiency can cause 75% of American adults to have at least one symptom of a sleep problem in the past year. 25% of American adults say that they do not get the minimum amount of sleep to be alert the next day. According to the latest analysis performed by the National Heart, Lung and Blood Institute, about 70 million people in the U.S. have a sleep problem and 40 million of these are chronic. Of these, 18 million people suffer from sleep apnea. Sleep related problems cause a cost of $18 billion per year as a result of reduced work performance and productivity. There is also immense potential in pediatric sleep monitoring as it accounts for 46% of the total market and has an annual growth of about 10% in revenue every year.

Current medical research relies on recordation of brainwaves to sort or determine the stages of sleep for an individual. Such equipment for brainwave recordation requires an individual to wear an uncomfortable cap or attached multiple electrodes with several wires connected to a nearby electronics box. These brainwaves are typically recorded overnight and analyzed by a sleep specialist to sort and score the sleep performance. There have been attempts to utilize wireless transmitters to reduce the need for wire connections; however, even in that case, wearing the cap or attaching electrodes can require some set-up time and professional expertise. In addition, the cap, even without wires, can be uncomfortable, and it is not usually available for home use. Accordingly, there is a need for improved systems and techniques for determining sleep patterns.

Further, a circadian rhythm is any physiological process that displays an endogenous, entrainable oscillation of about 24 hours. These rhythms are driven by a circadian clock, and rhythms have been widely observed in people, animals, and plants. Although circadian rhythms are endogenous ("built-in" or self-sustained), they are adjusted (entrained) to the local environment by external cues called zeitgebers, commonly the most important of which is daylight. In the case of a need for adjustment of an individual's circadian rhythm, a common approach is to control the exposure of the individual to lighting. However, there is a continuing need for improved systems and techniques for determining and controlling circadian rhythms.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are systems and methods for monitoring sleep. According to an aspect, a method includes emitting light into tissue. The method also includes detecting light backscattered from the tissue. Further, the method includes determining a sleep pattern based on the backscattered light.

According to another aspect, a method includes emitting light into tissue of a person. Further, the method includes detecting light backscattered from the tissue. The method also includes determining physiological parameters of the person based on the backscattered light. Further, the method includes determining a circadian rhythm of the person based on the physiological parameters.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
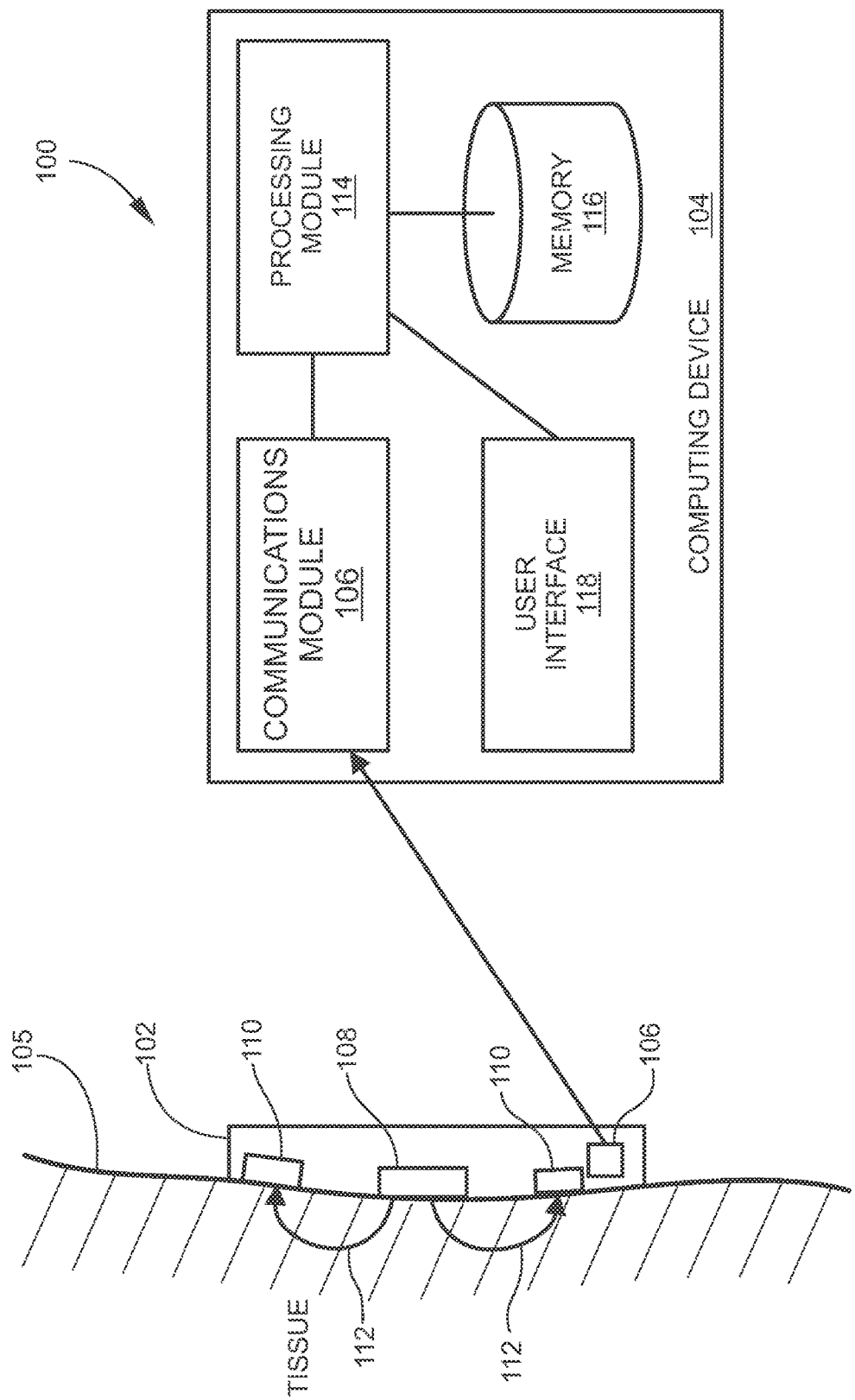
FIG. 1 is a schematic diagram of an example system for determining sleep patterns in accordance with embodiments of the present subject matter.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

As referred to herein, the term "computing device" should be broadly construed. For example, the computing device may be a mobile device such as, for example, but not limited to, a smart phone, a cell phone, a pager, a personal digital assistant (PDA, e.g., with GPRS NIC), a mobile computer with a smart phone client, or the like. A computing device can also include any type of conventional computer, for example, a desktop computer or a laptop computer. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats.

Recorded brainwaves are electrical signals generated by neurons, and these are coupled to the flow and circulation of blood (hemodynamic activity) in the brain to receive oxygen and nutrients for generation of required energy. Systems and methods in accordance with the present disclosure may monitor this blood flow or changes in its oxygen for sorting the stages of sleep. To sense blood (hemodynamic) activity, a system as disclosed herein may use a light source (e.g., a small, infrared light source), a light detector, and a set of near infrared spectroscopy-based algorithms to convert light information into blood flow or oxygenation information. For example, near infrared spectroscopy systems can be used to detect hemodynamic parameters, in particular oxygenated and deoxygenated hemoglobin concentration, for determining distinct patterns during different stages of sleep.

In accordance with embodiments of the present disclosure, a wearable device, such as a smart bandage (also referred to herein as the "SleepiBand") as described herein, may provide biophotonic analysis capability to enable miniaturized, low power, and low cost biophotonic brain monitoring. In an example, the wearable device or smart bandage may use BLUETOOTH® technology for providing wireless measurement of blood flow or oxygenation in the brain. In an example, the wearable device may include a two- or more wavelength, infrared light source (e.g., a light emitting diode (LED)) and a p-i-n photodiode connected to a system-on-chip microcontroller with an embedded transceiver (e.g., a cc2540 transceiver available from Texas Instruments). In an example operation, the cc2540 transceiver may send brief voltage pulses to an LED, which injects pulses of red and near infrared photons to the tissue. These photons are scattered back and comes out of the tissue after following a "banana" pattern. The detector can capture these photons and send a representative signal to the cc2540 transceiver for performing on-chip near infrared spectroscopy. Subsequently, this data may be transmitted to a nearby computing device such as a smartphone, tablet computer, or a stand-alone alarm clock. At a recipient computing device, the information may be utilized for further processing and control as described in further detail herein.

In accordance with embodiments, an alarm clock or a computing device application may receive data resulting from spectroscopy analysis for processing and control. In an example, the data may be stored at the alarm clock or computing device and used to make a user aware of his or her sleep stages. In this way, the user can monitor his or her sleep quality. In an example, an alarm clock can push the set time of the alarm clock forward or backward in time (e.g., 10-15 minutes ahead of or after a set time) such that the user can have a good sleep. In other words, the alarm time can be slightly adjusted to a better wake time based on the user's sleep activity or timing of sleep stages.

FIG. 1 illustrates a schematic diagram of an example system 100 for determining sleep patterns in accordance with embodiments of the present subject matter. Referring to FIG. 1, the system may include a wearable device 102 and a computing device 104. The wearable device 102 may be a "smart" bandage configured for wear by a person undergoing monitoring in accordance with embodiments of the present disclosure. For example, the wearable device 102 may include adhesive on at least one of its sides for attachment to a surface of the person's skin 105. The computing device 104 may be a mobile computing device such as, but not limited to, a smart phone and a tablet computer.

The wearable device 102 and the computing device 104 can be operative with one another. For example, the wearable device 102 and the computing device 104 may each include a communications module 106 for wireless communication with one another. For example, the communications module 106 may be configured to exchange data via BLUETOOTH® technology. Data collected and processed by the wearable device 102 as described by examples herein may be suitably communicated to the computing device 104 via the communication module 106 of the wearable device 102. Further, control data or other data generated by the computing device 104 may be suitably communicated to the wearable device 102. The wearable device 102 and the computing device 104 may include suitable hardware, software, and/or firmware for sending and communicating data.

It should be noted that although the wearable device 102 and the computing device 104 are described as being physically separated in examples disclosed herein, it should be understood that the devices can be implemented as one device for wear by a person. For example, the wearable device may include suitable hardware, software, and/or firmware for implementing the functionality of the computing device. In this case, the wearable device may be considered to include the computing device.

Although described in more detail by the examples set forth herein, the wearable device 102 may include a light source 108 for emitting light into tissue 105 and detectors 110 for detecting light backscattered from the tissue 105. The light may penetrate and be backscattered from any human tissue such as, but not limited to, the skin, scalp, skull, etc. Arrows 112 are represented of light emitted from the light source 108 and backscattered towards the detectors 110. The light source 108 may be a light emitting diode (LED) or any other suitable light source. The light source 108 may be configured to controllably emit red and/or infrared photons. Although this example depicts the wearable device 102 as including one light source, it should be understood that the wearable device 102 may include multiple light sources for emitting light into tissue.

The detectors 110 may be a detector of any suitable type that is positioned to detect the backscattered light 112 when the wearable device 102 is attached to skin. Example detectors include, but are not limited to, photodetectors, p-i-n or other photodiodes, photoresistors, phototransistors, charge-coupled-devices, and active pixel sensors. The detectors 110 may be configured to generate and output a signal representative of the backscattered light 112. The communications module 106 of the wearable device 102 may be configured to receive the signals from the detectors 110, and to suitably process and communicate the data to the computing device 104. Although the detectors 110 are shown as being on opposing sides of the light source 108, it is noted that the detectors 110 may be on the same side of the light source 108 and at any suitable distance.

The communications module 106 of the computing device 104 may receive the data representative of the backscattered light 112. Further, the communications module 106 of the computing device 104 may suitably process the received data and communicate it to a processing module 114. The processing module 114 may include hardware, software, and/or firmware for implementing the functionality disclosed herein. For example, the processing module 114 may include one or more processors and memory. Further, the computing device 104 may include memory 116 for storage of data for implementing the functionality disclosed herein.

The computing device 118 may include a user interface 118 for interaction with a user of the system 100. For example, the user interface 118 may be, but is not limited to, a display (e.g., touchscreen display), keyboard, mouse, or other device with which a user may interact. The user interface 118 may be utilized in accordance with examples described herein.

Figure 2:
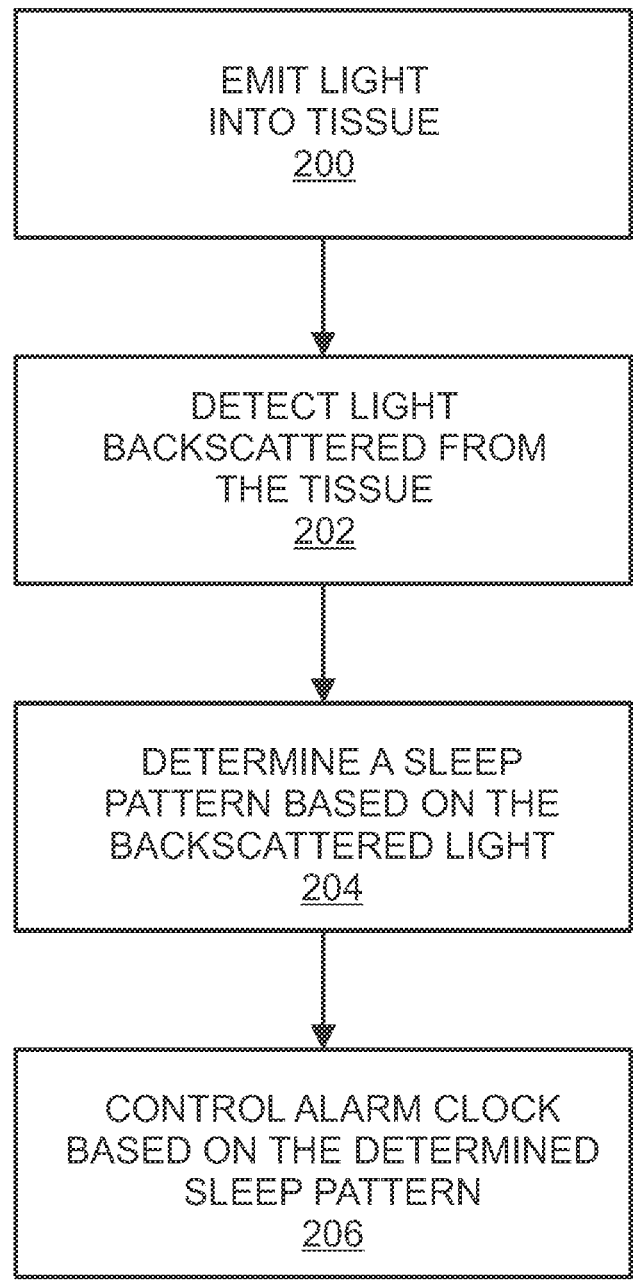
FIG. 2 is a flowchart of an example method for determining sleep stages in accordance with embodiments of the present disclosure.

FIG. 2 illustrates a flowchart of an example method for determining sleep stages in accordance with embodiments of the present disclosure. This method is described by example as being implemented by the system 100 shown in FIG. 1, although it should be understood that the method may be implemented by any other suitable system, computing device, or wearable device.

Referring to FIG. 2, the method includes emitting light into tissue (step 200). For example, the light source 108 may emit light into the skin 105. The user of the system 100 may interact with the user interface 118 for inputting a command to initiate control of the wearable device 102. The command may be received by the processing module 114, which in turn controls the communications module 106 to generate a command instruction for controlling the light source 108 to emit the light. The communications module 106 may communicate the command instruction to the wearable device 102. In response to receipt of the command instruction, the light source 108 may generate the light.

The method of FIG. 2 includes detecting light backscattered from the tissue (step 202). Continuing the aforementioned example, the detectors 110 may detect the backscattered light. As discussed by examples herein, the detectors 110 may generate a signal representative of the backscattered light and may communicate representative data to the computing device 104. The data may be received at the processing module 114.

The method of FIG. 2 includes determining a sleep pattern based on the backscattered light (step 204). Continuing the aforementioned example, the processing module 114 may determine a sleep pattern based on the data associated with the backscattered light. In one example, the processing module 114 may determine the sleep patter by determining hemodynamic parameters based on the data, and detecting sleep stages based on the determined hemodynamic parameters. In another example, the processing module 114 may determine a sleep pattern by determining hemodynamic patterns based on the detected light, and conducting brain electrical activity monitoring to be correlated or co-analyzed with determined hemodynamic parameters. Hemodynamic parameters may be detected or determined based on the detected light. Example hemodynamic parameters include, but are not limited to, heart rate, respiratory rate, cerebral oxygen saturation, and low frequency oscillations for diagnosing sleep disorders.

The method of FIG. 2 includes controlling an alarm clock based on the determined sleep pattern (step 206). Continuing the aforementioned example, the processing module 114 may generate and output signal for an alarm clock or other equipment based on the determined sleep pattern. For example, the computing device 104 may have an alarm clock residing thereon, and the alarm clock may be controlled to sound an alarm either before or after a preset alarm time based on the sleep pattern. The alarm may be reset to sound at a different time (e.g., 10 minutes before or after the preset alarm time) that is a better time for waking an individual. In another example, the alarm clock may be remote from the computing device, and the processing module 114 may control the communications module 106 to send a signal to the remote alarm clock for adjusting the alarm time.

Figure 3:
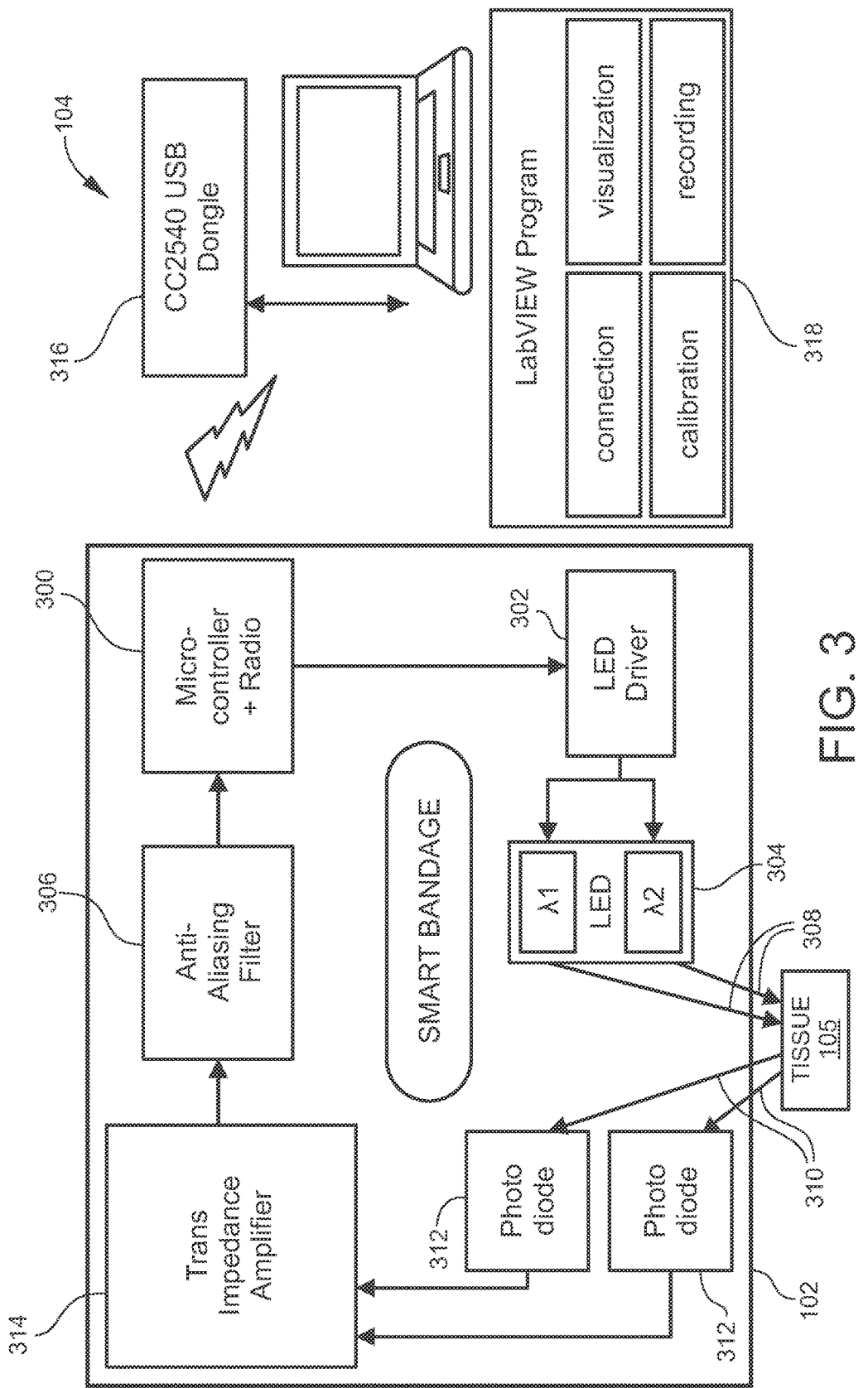
FIG. 3 is a block diagram of another example system for determining sleep patterns in accordance with embodiments of the present subject matter.

FIG. 3 illustrates a block diagram of another example system 300 for determining sleep patterns in accordance with embodiments of the present subject matter. Referring to FIG. 3, the system 300 includes a wearable device 102 and a computer device 104. The wearable device 102 may include a micro-controller and radio 300. The micro-controller may be configured to implement functionality for controlling an LED driver 302 and LEDs 304, for receiving signals from an anti-aliasing filter 306, and for controlling the radio to communicate with the computing device 104.

As an example of the operation of the wearable device 102, the micro-controller may communicate control signals to the LED driver 302 for turning on the LEDs 304, which may then emit light 308 into tissue 105. Light 310 backscattered from the tissue 105 may be received by photodiodes 312 or another suitable detector. In turn, the photodiodes 312 may generate a signal representative of the backscattered light 310 and communicate the signal to a trans-impedance amplifier 314 and the filter 306 for conditioning. The micro-controller and radio 300 may process the signal for communication to the computing device 104. For example, themicro-controller and radio 300 may wirelessly communicate the data to a USB dongle 316 attached to the computing device 104 and configured to receive the wireless communication. The signal may be communicated by use of, for example, a BLUETOOTH® communication technique. The computing device 104 may be implement the LabVIEW program 318 for determining a sleep pattern based on the received data and for implementing other functionality as described herein. For example, the program 318 may be configured to implement functionality for viewing the data, calibrating the wearable device 102, and recording the data.

Figure 4:
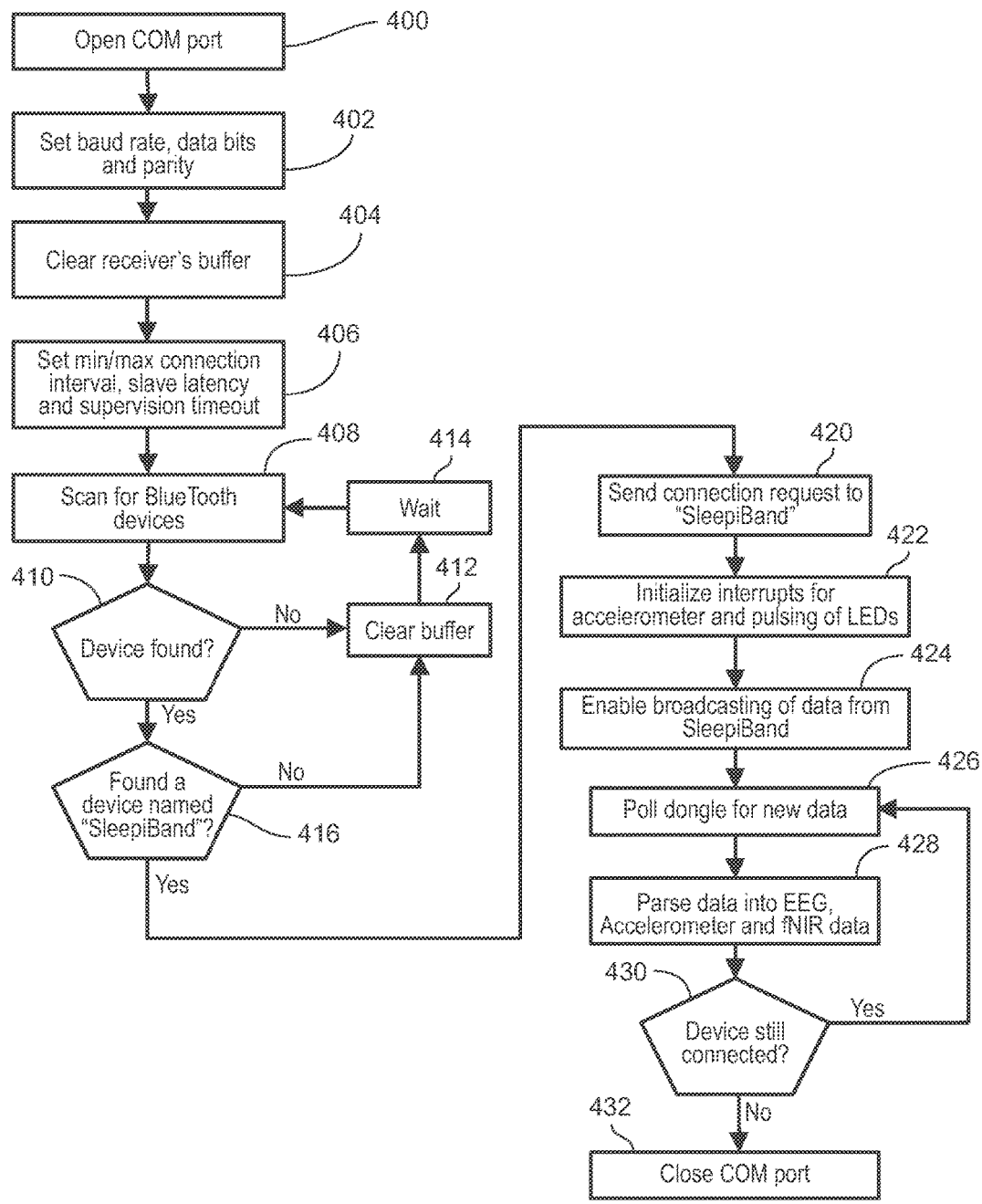
FIG. 4 is a flowchart of an example method for establishing and managing communications between a computing device and wearable device in accordance with embodiments of the present disclosure.

FIG. 4 illustrates a flowchart of an example method for establishing and managing communications between a computing device and wearable device in accordance with embodiments of the present disclosure. This method is described by example as being implemented at the system shown in FIG. 3, although it should be understood that the method may be implemented by any other suitable system or by any suitable computing device.

The method of FIG. 4 may start with step 400 by opening a communication (COM) port. For example, the computing device 104 shown in FIG. 3 may open one of its communication ports. Subsequently, the method includes setting the baud rate, data bits, and parity for the opened COM port (step 402) and clear the associated receiver's buffer (step 404). The method also includes setting a minimum and maximum connection interval, slave latency, and supervision timeout (step 406). The computing device 104 may suitably set these parameters.

The method of FIG. 4 includes scanning for BLUETOOTH® devices. For example, the computing device 104 may scan for devise compatible with BLUETOOTH® version 4.0, such as the wearable device 102. The method also includes determining whether the BLUETOOTH® device is found (step 410). In response to determining that the device is not found, the buffer may be cleared (step 412) and the computing device may continue to wait (step 414) until a BLUETOOTH® device is found.

Continuing with FIG. 4, the method includes determining whether a device named "Sleepiband" is found. For example, the wearable device 102 shown in FIG. 3 may be named "Sleepiband". It is noted that a device of any other name may be searched in order to apply methods in accordance with the present disclosure. In response to determining to that the device named "Sleepiband" is not found, the method may proceed to step 412 and so forth following step 412.

In response to determining that a device named "Sleepiband" is found at step 416, the method may proceed with steps for establishing a connection with the device and for managing the connection. At step 418, the computing device 104 may send a connection request to the "Sleepiband" device (step 420). In this example, the "Sleepiband" device may be wearable device 102. Subsequently, the computing device 104 may initialize interrupts for an accelerometer and pulsing of LEDs for the "Sleepiband" device (step 422).

Further, the computing device 104 may enable broadcasting of data from the "Sleepiband" device (step 424) and poll a dongle attached to the computing device 104 for new data received from the "Sleepiband" device (step 426). The data may be data relating to electroencephalography (EEG), an accelerometer, and fNIR data. The data may be parsed at step 428. Further, the method may include determining whether the "Sleepiband" device is still connected (step 430). While the device is connected, the method may proceed through the loop of steps 426, 428, and 430 to collect data from the wearable device 102. In response to determining that the device is not connected, the communication port may be closed (step 432).

Figure 5:
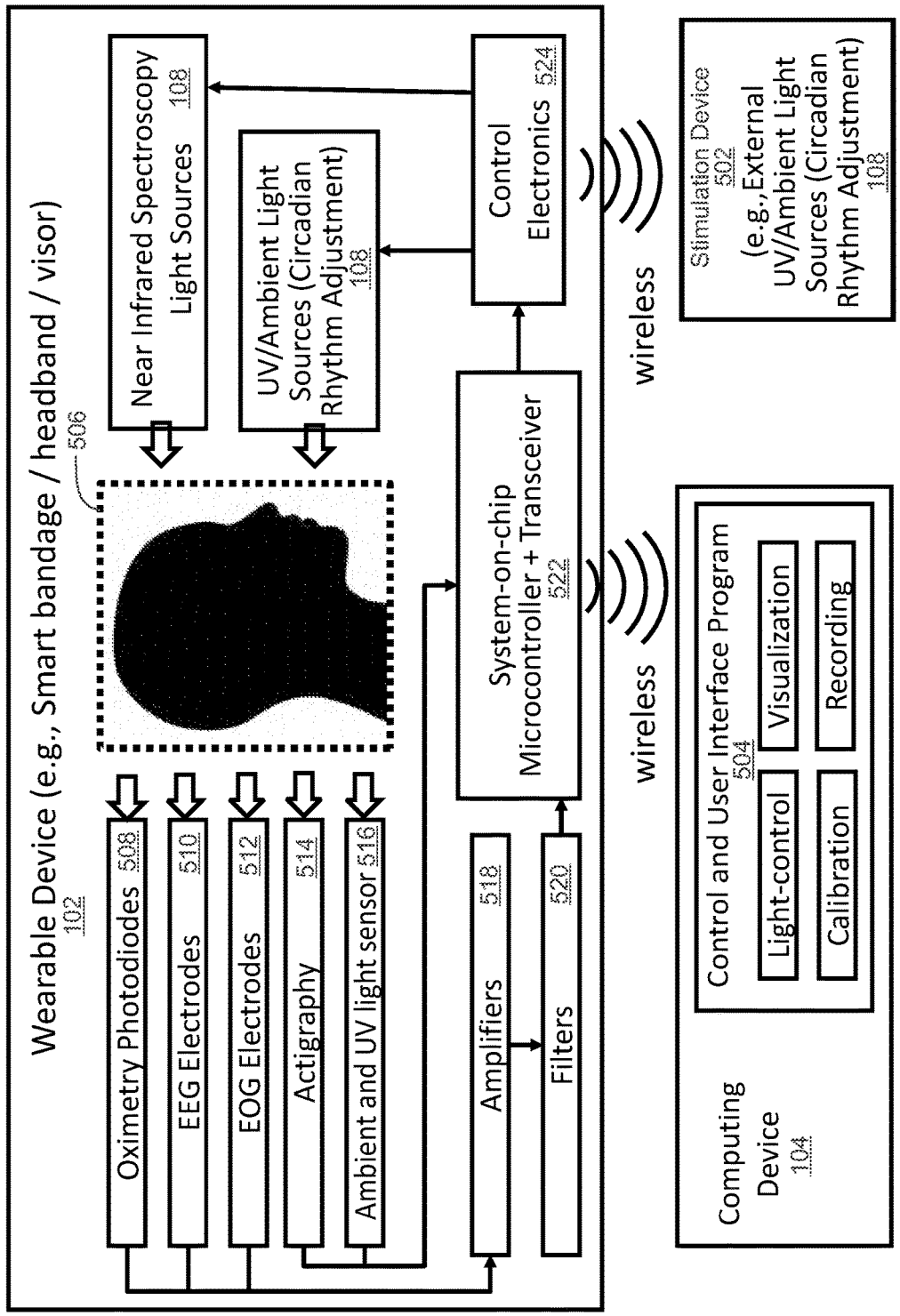
FIG. 5 is a block diagram of an example system for determining a circadian rhythm in accordance with embodiments of the present disclosure.

In accordance with embodiments of the present disclosure, light backscattered from the tissue of a person and/or other signals indicating physiological parameters may be used for determining an estimation of circadian rhythm of the person. For example, FIG. 5 illustrates a block diagram of an example system 500 for determining a circadian rhythm in accordance with embodiments of the present disclosure. The system 500 may include a wearable device 102, a computing device 104, and a stimulation device 502. The wearable device 102 and the computing device 104 may include functionality as described by examples set forth here. Further, the computing device 104 may include a control and user interface program 504 residing thereon for light-control of the wearable device 102, calibration, visualization, and recording. The wearable device 102 and the computing device 104 may be configured for wireless communication with each other for control of the wearable device 102 by the computing device 104 and for the communication of data gathered by the wearable device 102 to the computing device 104 for processing.

The wearable device 102 may include multiple components for determining physiological parameters of a person 506. Particularly, the wearable device 102 may include oximetry photodiodes 508, EEG electrodes 510, EOG electrodes 512, an actigraphy device 514, and an ambient and UV light sensor 516 for collecting data associated with physiological parameters of the person 506. The components may be suitable configured in the wearable device 102 and positioned for capturing the data. The data may be suitable conditioned. For example, the output of the photodiodes 508 and the electrodes 510 and 512 may be input to amplifiers 518 and filters 520 for conditioning. The output signals may be received at a system-on-chip microcontroller and transceiver 522 for processing and for communication of a signal representative of the processed data to the computing device 104. The data may be suitably packaged by the microcontroller and transceiver 522 for wireless communication to the computing device 104.

Continuing with the operation of the wearable device 102, the microcontroller and transceiver 522 may generate and communicate control instructions to control electronics 524 for control of one or more light sources 108. In this example, the light sources include near infrared spectroscopy light sources and UV/ambient light sources, although it should be understood that any suitable light sources or other stimulation devices may be utilized. The control electronics 524 may include hardware, firmware, software, and/or combinations thereof for receiving control instructions from the microcontroller and transceiver 522 and for sending control signals to the light sources 108. The light sources may reside on the wearable device and/or may be remote devices configured to receive wirelessly-communicated, control signals sent by the control electronics 524. The light sources 108 may emit light into tissue of the person 506 for detection of the backscattered light from the tissue by the photodiodes 508. Further, the ambient and UV light sensor 516 may detect the UV/ambient light generated by those light sources 108.

Figure 6:
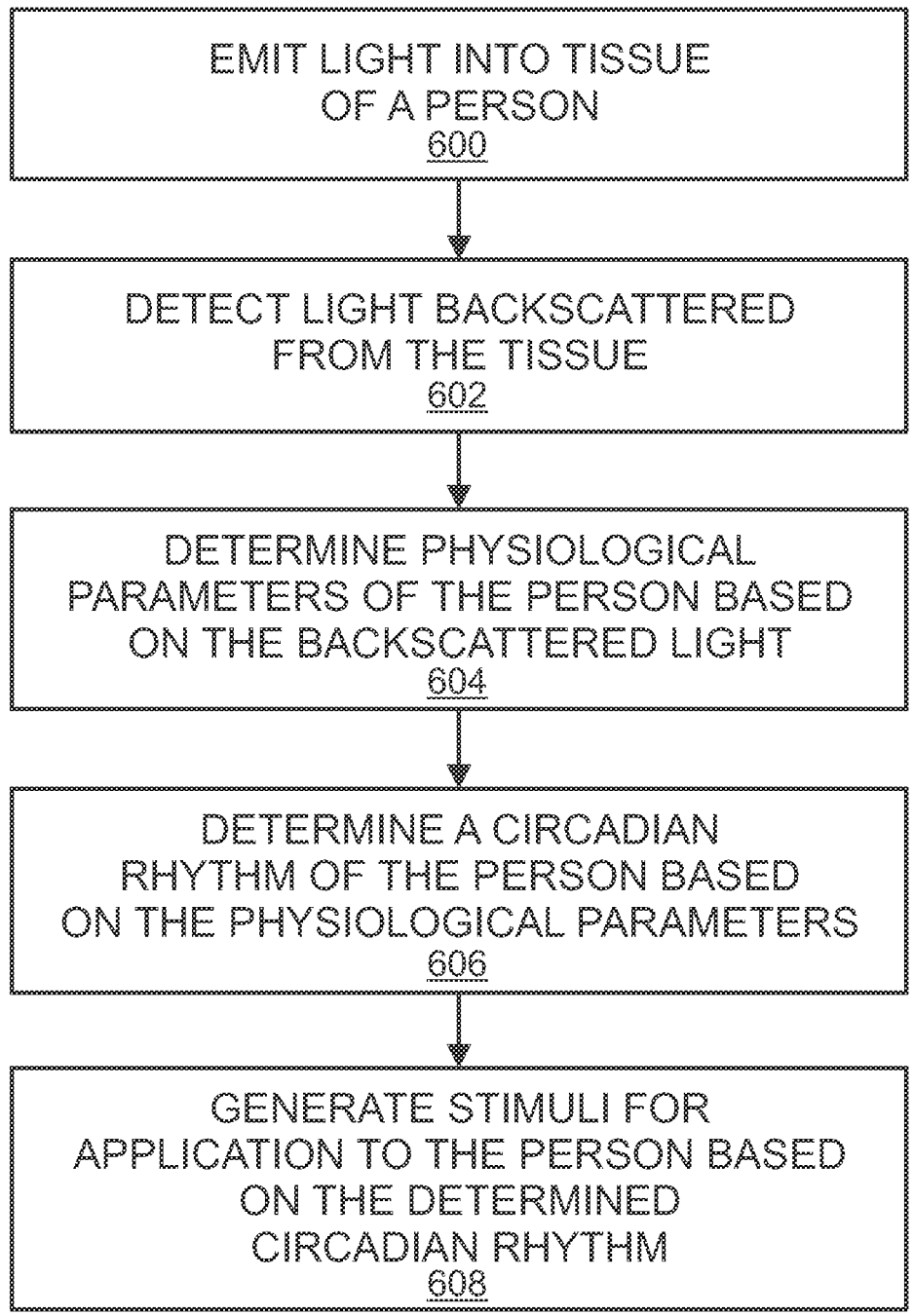
FIG. 6 is a flowchart of an example method for determining a circadian rhythm in accordance with embodiments of the present disclosure.

FIG. 6 illustrates a flowchart of an example method for determining a circadian rhythm in accordance with embodiments of the present disclosure. The method is described as being implemented by the system 500 shown in FIG. 5, although it should be understood that the method may alternatively be implemented by any other system. Referring to FIG. 6, the method includes emitting light into tissue of a person (step 600). For example, the microcontroller and transceiver 522 and control electronics 524 may control the light sources 108 to generate light and emit light into tissue of the person 506. The light emitted may include near infrared spectroscopy (low frequency hemodynamic oscillations) signals.

The method of FIG. 6 also includes detecting light backscattered from the tissue (step 602). Continuing the aforementioned example, the photodiodes 508 may detect the backscattered light. Further, the UV/ambient light sources 108 may generate UV/ambient light that is detected by the ambient light and UV light sensor 516. This collected data may be output and conditioned by the amplifiers 518 and filters 520. The conditioned data may then be communicated to the computing device 104 by the microcontroller and transceiver 522.

Continuing with FIG. 6, the method includes determining physiological parameters of the person based on the backscattered light (step 606) and determining an estimation of circadian rhythm of the person based on the physiological parameters (step 608). Continuing the aforementioned example, the computing device 104 may determine physiological parameters via the backscattered light and determine an estimation of circadian rhythm based on computational models that relate circadian rhythm to these parameters. Further, for example, the computing device 104 may receive and combine other data detected by the photodiodes 508, electrodes 510 and 512, actigraphy device 514, and the light sensor 516 for use in determining the physiological parameters and for determining an estimation of the circadian rhythm. Another example physiological parameter that may be detected and determined includes body temperature. The computing device may also receive data related to environmental parameters such as ambient temperature, oxygen or carbondioxide content of the air, or intensity and spectrum of the ambient light. These parameters may be used for more accurate estimation of the circadian rhythm.

The method of FIG. 6 also includes generating stimuli for application to the person based on the determined circadian rhythm (step 608). Continuing the aforementioned example, the computing device 104 may determine control signals to adjust and control the circadian rhythm estimated from hemodynamic signals measured via the light sources and detectors. The control signals may be wirelessly communicated to the wearable or portable device 102 for the generation of UV/ambient stimuli light by the light sources 108 for application to the person 506 for adjustment of his or her circadian rhythm. The control signals may also change other environmental parameters such as ambient temperature via air conditioning systems or oxygen or carbondioxide content of the air.

It is noted that the process implemented by the system 500 shown in FIG. 5 and the method of FIG. 6 or a similar process may be implemented continuously. For example, the process may be implemented during daily life activities of a person for circadian rhythm monitoring and adjustment. In an example, light may be used as described herein for simulating the person to adjust the circadian rhythm. A mobile computer, smartphone, or other microcontroller based system may couple physiological sensing received from a wearable device to the external photic control device. A circadian rhythm estimation model and circadian pacemaker control algorithm in accordance with the present disclosure can close the loop between the light exposure and physiological sensing devices to diagnose and treat circadian misalignment. The disruption of circadian rhythm may trigger degrading sleep disorders. A system and method in accordance with the present disclosure may be used to efficiently track the circadian rhythm and its outcome on an individual's sleep performance (sleep/wake cycle and quality of sleep).

The present subject matter can provide a low cost, low power, low noise, miniaturized, wireless system for automated assessment of sleep physiology addressing the shortcomings of currently existing systems. This is achieved by expanding the types of physiological signal assessments carried out to include near infrared spectroscopy to provide the capacity to detect changes in brain oxygenation and to better reflect sleep stage-related changes in brain function. NIRS also provides heart rate and breathing rate estimates for assessment and detection of events of interest such as apneas.

As an example, a central systems based approach is provided as follows: (1) adaptive signal processing applied to system-on-chip based NIRS measurements allows enough signal to noise ratio for a single light emitting diode (LED)-photodetector pair to simultaneously monitor multiple hemodynamic parameters (heart rate (HR), respiratory rate (RR), low frequency oscillations (LFO)) relevant to sleep physiology; (2) the wireless bandage technology is more comfortable and disturbs sleep less than traditional PSG systems; (3) a smart bandage allows machine learning algorithms to be applied to data from multiple sensors (NIRS, electroencephalography (EEG), electromyography (EMG), electrooculography (EOG)) to provide feature representations unique to specific sleep stages and events (such as apneas) and allow comparable or better detection of events and sleep stages than traditional systems with reduced number of sensors. Therefore, a smart bandage can lead to improved capacity to carry out sleep research and to detect and treat sleep disorders. The miniaturization and high signal-to-noise-ratio (SNR) paves the way for rapid adoption and deployment of these bandages for home-use in real-world settings. Given the high prevalence and substantial impairments associated with sleep disorders, a smart bandage as described herein has the potential to have a major positive impact on public health.

A smart bandage, as disclosed herein, can incorporate commercial off the shelf (COTS) system-on-chip (SoC) microcontrollers or other suitable systems with embedded transceivers for a low-cost, wireless, miniaturized system in the form factor of an adhesive bandage which disturbs and limits subjects to a far lesser degree than traditional PSG systems. The presently disclosed system can expand the types of sleep efficiency assessment carried out to include near-infrared-spectroscopy (NIRS) in order to measure multiple parameters simultaneously, and provide improved analysis capacity: the frequency analysis of spontaneous oxygenated hemoglobin (oHb) and deoxygenated hemoglobin (dHb) oscillations provides heart rate (HR) and respiratory rate (RR) data, where the phase difference between oHb and dHb changes at lower frequencies provides a mean to improve the differentiation of sleep stages.

Performance of NIRS during "sleep" improves the signal to noise ratio (SNR) with respect to the standard NIRS with awake patients due to the relatively decreased amount of head movement. A smart bandage may incorporate inertial measurement units (IMU), additional photodiodes, and adaptive signal processing to remove artifacts and further improve the SNR. This improved SNR can provide NIRS the ability to detect brain hemodynamic changes more accurately increasing the detection sensitivity of sleep-apnea related events and to better reflect sleep-related changes in brain function, thereby improving the correlation between sensor-measurement-derived and self-reported indices of sleep. Further, improvement in power consumption is achieved with the use of COTS proximity sensors as light detectors and supporting electronic circuits to reduce the cost and size of the system. Further, the smart bandage is capable of recording EEG, electromyography (EMG), electrooculography (EOG), and head motion as in the case of traditional PSG system, but in much smaller form factors. However, the inclusion of NIRS in a smart bandage can help reduce the number of EEG channels in addition to providing the capability of eliminating the EMG and EOG electrodes altogether to further miniaturize the system. The multi-model sensing capability (NIRS, EEG, EMG, EOG, and IMU) provided by a smart bandage enables multivariate machine learning based classification methods to isolate and discover the NIRS features that characterize and detect various sleep stages. This characterization, in turns, can let NIRS replace EMG and EOG sensing without any reduction in SNR, sensitivity or specificity. Therefore, the NIRS capability of the mart bandage can provide capability not only to detect hemodynamic parameters (heart rate, respiratory rate) for sleep-apnea detection, but also to reduce the number of biopotential (EEG, EMG, and EOG) for accurate sorting of sleep stages and assessing sleep efficiency and quality. By improving the methodology for assessing sleep physiology, a smart bandage as described herein has the potential to lead to improved capacity to carry out sleep research and diagnose and treat sleep disorders.

In accordance with embodiments, a system for monitoring sleep activity as disclosed herein can take simultaneous measurements of three hemodynamic oscillations: arterial pulsations, respiratory rate synchronized oscillations and the low frequency oscillations (LFO), and the last as an indicator of sleep stages. The smart bandage can enable studies to correlate NIRS with EEG recordings during sleep to further investigate the relation between these two modality. For this, the system can provide a dashboard of relevant sensor information such as heart rate (HR), respiratory rate (RR), hemodynamic LFO, cerebral arterial oxygen saturation, EEG, EOG, EMG and inertial measurement data. This telemetry system consists of two major components: (1) a system-on-chip (SoC) based sensor-interfacing and data acquisition hub with wireless transceiver (smart bandage), and (2) a remote base station to record and analyze the collected data. Real-time machine learning inference algorithms on the base-station would provide further capacity to obtain an objective correlation between NIRS and biopotential measurements. The smart bandage sensors, sensor interfaces and transceiver leverage low cost and low-power COTS components; are built on a miniaturized flexible printed circuit board (PCB); and contain a COTS rechargeable battery and antenna unit for short range signal transmission. The smart bandage can combine multiple sensors in the form factor of an adhesive bandage that consumes little enough power to rely on a light weight lithium polymer battery as the power source throughout an over-night data collection session.

Adaptive signal processing techniques enable the achievement of sufficient SNR to be able to extract acceptable heart rate, respiratory rate, arterial saturation and low frequency oscillation parameters from the NIRS signal to reduce or eliminate EEG, EOG, EMG sensors.

For inertial measurements, a COTS MEMS-based ultra-low power accelerometer can be connected to a COTS SoC integrated circuit (IC) incorporating a microcontroller and BLUETOOTH® communication technology. A COTS multiwavelength LED and photodiode with on-board transimpedance amplifier are connected to SoC IC to provide NIRS data. This system can perofmr continuous wave measurement; the most common NIRS modality enabling measurements of relative changes in oHb and dHb concentrations. For spectral analysis, multiwavelength LED is time multiplexed by pulses provided by the SoC microcontroller. The back-scattered photons are received by the photodiode. The SoC IC either performs the NIRS on board and transmits the processed data or transmit raw data. Instrument amplifiers are also incorporated to the SoC IC to include electrophysiological (EMG, EEG, and EOG) signal recording. Standard silver/silver-chloride leads are connected to the PCB through soldered mini-connectors. Frequency analysis performed on NIRS signal either on the SoC IC or on the base station computer is used to detect the HR and RR. The pulse oximetry analysis provides the cerebral arterial oxygen saturation.

To reduce the size and power consumption, two optional COTS proximity sensors can be incorporated to the smart bandage. These sensors come with on-board adjustable LED drivers and infrared photo-detectors integrated into ultra-miniature sizes. Two sensors can be located at two different distances (around 1 cm and 2 cm) to sense the back-scattered photons from multiple depths. A differential measurement between these two photodiodes reduces the effect of the superficial layers (scalp muscles and skin) to focus the recording on the cortical layer, and thereby increasing the SNR. Another optional improvement is through the use of COTS LEDs with an internal photodiode located in the same package to measure the reflected light directly from the skin. This data can be used to correct the drift in the LED output and the artifacts caused by motion and the contraction of the facial muscles on the forehead. To further improve the SNR, the inertial sensor data is used in adaptive noise cancellation to compensate for motion artifacts when the subject is moving in the bed. Active noise cancellation (ANC) algorithm and techniques are adopted where the accelerometer signal and/or internal photodiodes output serve as a noise reference input to be correlated to the motion-induced noise signal.

A smart bandage in accordance with embodiments of the present subject matter can introduce NIRS measurements to standard PSG with an aim of hardware miniaturization and power reduction for more practical sensor systems for sleep studies. The sleep stage identifying NIRS parameters are extracted through the use of the Sleepiband device described herein. This can be achieved by the use of supervised learning based classification methods to isolate and identify the distinct features in NIRS signals (in particular hemodynamic LFO) by using the multivariate time series data to identify sleep stages and clinically-important sleep events. This enables the extraction of distinct features of NIRS data, especially LFO of oHb and dHb, for each sleep stage. The pattern classifiers are used for an objective assessment of how each sensor parameter can improve the sleep stage and event identification accuracy.

A two-stage process can be followed to extract and select the features before training the classification algorithms. Experienced scorers of PSG data can identify the sleep stages and events following standard guidelines. This is then be used to train feature extraction algorithms to extract several features from EEG, EOG, NIRS (HR, RR, LFO) and IMU signals by using Hjorth complexity parameters, power spectrum and histogram based waveform measures. The distinct features in low-frequency hemodynamic oscillations during various stages/events, such as the NIRS recorded phase shift between LFO of oHb and dHb, are also generated by this analysis. This can enable the discovery of new useful feature representations. Moreover, the output of these three feature extraction schemes can be inputted to two different pattern classifiers (support vector machine, k-nearest neighbor (k-NN) classifier) to generate sleep hypnograms to be compared by the ones generated by scoring the raw data. Feature extractors and pattern classifiers are used to "objectively" assess the contribution of each smart bandage parameter (NIRS based HR, RR, LFO, arterial saturation, EOG, each EEG channel, head movement) in the discrimination of sleep and wake states as well as identification of clinically-important sleep events. This analysis is used to eliminate some of the sensors when not needed to minimize device complexity and power consumption.

Systems, devices, and methods in accordance with the present subject matter can combine hemodynamic analysis with brainwave measurements and activity monitoring in the form factors of an adhesive bandage for accurate detection of sleep stages. It may also incorporate heartbeat rate and respiratory rate variability to these measurements to improve the accuracy even further and also enables sleep apnea tracking This can make the present subject matter desirable for tracking sleep for self-management of health and also as a research tool for sleep and sleep apnea laboratories. Further, wireless capability as described herein can offer low-power operation for an extended battery life and also provide communication with nearby smartphones, computer, or standalone electronic units such as smart alarm clocks.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A method utilizing brain monitoring, the method comprising:
    determining a sleep pattern using a wireless smart bandage including a system-on-a-chip, the system-on-a-chip including a microcontroller and a transceiver;
    emitting, by a light source of the wireless smart bandage, light having two or more wavelengths into tissue, wherein the light source is controlled by the microcontroller via the transceiver;
    detecting, by a light detector of the wireless smart bandage, light backscattered from the tissue, wherein the light detector is communicatively coupled to the microcontroller via the transceiver and sends a signal representative of the backscattered light to the microcontroller via the transceiver;
    performing, at the wireless smart bandage by the microcontroller of the system on a chip, near infrared spectroscopy analysis based on the signal representative of the backscattered light; and
    wirelessly transmitting, via the transceiver of the system-on-a-chip, hemodynamic parameter data of a brain that is based on the near infrared spectroscopy analysis to a computing device for determining a sleep pattern based on the backscattered light.

2. The method of claim 1, wherein the light includes red and near infrared photons.

3. The method of claim 1, wherein emitting light by a light source of the wireless smart bandage includes using a light emitting diode (LED) of the wireless smart bandage to emit the light having two or more wavelengths.

4. The method of claim 1, wherein detecting light by a light detector of the wireless smart bandage includes using one or more detectors comprising of a photodiode, a photoresistor, a phototransistor, a charge-coupled-device, or an active pixel sensor of the wireless smart bandage to detect the backscattered light.

5. The method of claim 1,
    wherein the computing device is a remote computing device, a computing device included within the wireless smart bandage, a smart phone, a tablet computer, or an alarm clock.

6. The method of claim 1, wherein determining a sleep pattern based on the backscattered light comprises determining the sleep pattern or a sleep disorder at the computing device utilizing the hemodynamic parameter data of the brain that is based on the near infrared spectroscopy analysis performed at the system-on-a-chip of the wireless smart bandage.

7. The method of claim 1, wherein the steps of emitting and detecting are implemented at the wireless smart bandage and the wireless smart bandage has a bandage form factor and is attachable to a forehead skin surface.

8. The method of claim 1, further comprising generating, by the computing device, a control signal for controlling the emission of light.

9. The method of claim 1, further comprising controlling, by the computing device, an alarm time of an alarm clock or other equipment based on the hemodynamic parameter data of the brain.

10. The method of claim 1, wherein determining a sleep pattern based on the backscattered light comprises:
    determining the hemodynamic parameter data of the brain based on the detected light using near infrared spectroscopy; and
    detecting sleep stages or sleep disorders based on the determined hemodynamic parameters data of the brain.

11. The method of claim 1, wherein determining a sleep pattern based on the backscattered light comprises:
    determining the hemodynamic parameters data of the brain based on the backscattered light; and
    conducting brain electrical activity monitoring and actigraphy to be correlated or co-analyzed with the determined hemodynamic parameter data of the brain.

12. The method of claim 1, further comprising detecting, by the wireless smart bandage, the hemodynamic parameter data of the brain based on the near infrared spectroscopy analysis.

13. The method of claim 12, wherein the hemodynamic parameter data of the brain that is determined using the near infrared spectroscopy represents one or more of changes in oxygenated and deoxygenated hemoglobin concentration in the brain, cerebral tissue oxygen saturation, low frequency oscillations of cerebral oxygenation, and cerebral arterial pulsations for determining sleep stages or diagnosing sleep disorders.

14. A system utilizing brain monitoring, the system comprising:
a wireless smart bandage including:
a system-on-a-chip having a microcontroller and a transceiver;
a light source communicatively coupled to the microcontroller via the transceiver, the light source configured to emit light having two or more wavelengths into tissue, wherein the light source is controlled by the microcontroller; and
a light detector communicatively coupled to the microcontroller via the transceiver, the light detector configured to detect light backscattered from the tissue and send a signal representative of the backscattered light to the microcontroller; wherein
the microcontroller of the wireless smart bandage performs near infrared spectroscopy based sleep pattern analysis based on the signal representative of the backscattered light to determine hemodynamic parameter data of a brain, and wirelessly transmits, via the transceiver, the hemodynamic parameter data of the brain to a computing device configured to determine and further analyze a sleep pattern based on the hemodynamic parameter data of the brain.

15. The system of claim 14, wherein the wireless smart bandage has a bandage form factor and is attachable to a forehead skin surface by itself or as a part of a headband.

16. The system of claim 14, wherein the light includes red and near infrared photons.

17. The system of claim 14, wherein the light source includes a light emitting diode (LED) configured to emit the light having two or more wavelengths.

18. The system of claim 14, wherein the wireless smart bandage includes one or more detectors configured to detect the light, the one or more detectors including a photodiode, a photoresistor, a phototransistor, a charge-coupled-device, or an active pixel sensor of the wireless smart bandage.

19. The system of claim 14, wherein the
computing device is a remote computing device, a computing device included within the wireless smart bandage, a smart phone, a tablet computer, or an alarm clock.

20. The system of claim 14, wherein the computing device is configured to generate a control signal for controlling the emission of light.

21. The system of claim 14, wherein the computing device is configured to control an alarm time of an alarm clock or other equipment based on the data of the near infrared spectroscopy analysis sleep pattern analysis.

22. A method utilizing brain monitoring, the method comprising:
estimating a circadian rhythm of a person using a wireless smart bandage including a system-on-a-chip, the system-on-a-chip including a microcontroller for controlling the wireless smart bandage and a wireless transceiver;
emitting, by a light source of the wireless smart bandage, light into tissue of a person;
detecting, by light sensors of the wireless smart bandage, light backscattered from the tissue, the light sensors including a cerebral oximetry detector and an ambient and ultra-violet light sensor, and communicating data representing the backscattered light to the microcontroller of the system-on-a-chip;
determining, by a computing device, cerebral hemodynamic parameters of the person based on near infrared spectroscopy analysis of the backscattered light received via the wireless transceiver; and
determining, by the computing device, an estimation of circadian rhythm of the person based on the cerebral hemodynamic parameters and computational models that relate the circadian rhythm to the cerebral hemodynamic parameters.

23. The method of claim 22, wherein the light includes red and near infrared photons.

24. The method of claim 22, wherein emitting light includes using a light emitting diode (LED) of the wireless smart bandage to emit the light.

25. The method of claim 22,
wherein the computing device is a remote computing device, a computing device included within the wireless smart bandage, a smart phone, a tablet computer, or a photic control device for adjusting a circadian rhythm.

26. The method of claim 25, wherein the steps of emitting and detecting are implemented at the wireless smart bandage that has a bandage form factor and is attachable to a forehead skin surface by itself or as a part of a headband or visor.

27. The method of claim 22, further comprising generating, by the computing device, a control signal for controlling the emission of light.

28. The method of claim 22, wherein the cerebral hemodynamic parameters determined using the near infrared spectroscopy comprise one or more of changes in oxygenated and deoxygenated hemoglobin concentration in the brain, cerebral tissue oxygen saturation, low frequency oscillations of cerebral oxygenation, and cerebral arterial pulsations to estimate the circadian rhythm.

29. The method of claim 22, further comprising generating stimuli for application to the person based on the estimated circadian rhythm of the person from the analysis of light backscattered using near infrared spectroscopy.

30. The method of claim 29, wherein generating the stimuli comprises generating stimuli light by a photic control device based on a signal transmitted from the wireless smart bandage via the wireless transceiver.

31. The method of claim 29, wherein generating the stimuli comprises generating stimuli light by a photic control device based on a signal transmitted from the wireless smart bandage via the wireless transceiver.

32. The method of claim 22, wherein estimating circadian rhythm based on the backscattered light from the tissue comprises:
determining hemodynamic parameters based on the backscattered light; and
conducting brain electrical activity monitoring and actigraphy to be correlated or co-analyzed with the determined hemodynamic parameters.

33. A system that utilizes brain monitoring, the system comprising:
a wireless smart bandage including a system-on-a-chip that has a microcontroller for controlling the wireless smart bandage and a transceiver;
a light source of the wireless smart bandage that is communicatively coupled to the microcontroller, the light source configured to emit light into tissue; and
light sensors of the wireless smart bandage communicatively coupled to the microcontroller, the light sensors configured to detect light backscattered from the tissue and communicate data representing the backscattered light to the microcontroller of the system-on-a-chip, the light sensors including an oximetry detector and an ambient and ultra-violet light sensor of the wireless smart bandage; and a computing device configured to:
  determine cerebral hemodynamic parameters of a person based on the backscattered light from the tissue using near infrared spectroscopy; and
  determine an estimation of circadian rhythm of the person based on the cerebral hemodynamic parameters and computational models that relate the circadian rhythm to the cerebral hemodynamic parameters.

34. The system of claim 33, wherein the light includes red and near infrared photons.

35. The system of claim 33, wherein the wireless smart bandage includes a light emitting diode (LED) for emitting the light.

36. The system of claim 33, wherein the computing device is a remote computing device, a computing device included within the wireless smart bandage, a smart phone, a tablet computer, or a photic control device for adjusting a circadian rhythm.

37. The system of claim 33, wherein the computing device is configured to generate a control signal for controlling the emission of light.

38. The system of claim 33, wherein the cerebral hemodynamic parameters determined using the near infrared spectroscopy comprise one or more of changes in oxygenated and deoxygenated hemoglobin concentration in the brain, cerebral tissue oxygen saturation, low frequency oscillations of cerebral oxygenation, and cerebral arterial pulsations to estimate the circadian rhythm.

39. The system of claim 33, further comprising a stimulation device configured to generate stimuli for application to the person based on the estimated circadian rhythm of the person from the analysis of light backscattered from the tissue using near infrared spectroscopy.

40. The system of claim 39, wherein the stimulation device is configured to generate stimuli light based on a signal transmitted from the wireless smart bandage via the wireless transceiver.

* * * * *